(12) United States Patent
Kiguchi

(10) Patent No.: US 10,537,102 B2
(45) Date of Patent: Jan. 21, 2020

(54) SYNERGISTIC FUNGICIDAL COMPOSITION FOR CONTROLLING PLANT DISEASES

(71) Applicant: Sumitomo Chemical Company, Limited, Tokyo (JP)

(72) Inventor: So Kiguchi, Takarazuka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 16/081,967

(22) PCT Filed: Mar. 10, 2017

(86) PCT No.: PCT/JP2017/009710
§ 371 (c)(1),
(2) Date: Sep. 4, 2018

(87) PCT Pub. No.: WO2017/155086
PCT Pub. Date: Sep. 14, 2017

(65) Prior Publication Data
US 2019/0037847 A1    Feb. 7, 2019

(30) Foreign Application Priority Data

Mar. 11, 2016 (JP) ................................. 2016-048171

(51) Int. Cl.
*A01N 43/713*    (2006.01)
*A01N 43/56*    (2006.01)

(52) U.S. Cl.
CPC ........... *A01N 43/713* (2013.01); *A01N 43/56* (2013.01)

(58) Field of Classification Search
CPC ...... A01C 1/06; A01N 43/653; A01N 43/707; A01N 43/713
See application file for complete search history.

(56) References Cited

U.S. PATENT DOCUMENTS

| | | |
|---|---|---|
| 2014/0011852 A1 | 1/2014 | Venturini et al. |
| 2015/0051171 A1 | 2/2015 | Yoshimoto et al. |
| 2015/0164076 A1 | 6/2015 | Pellacini et al. |
| 2016/0150788 A1 | 6/2016 | Matsuzaki |
| 2016/0165890 A1* | 6/2016 | Matsuzaki ........... A01N 43/713 514/255.06 |

FOREIGN PATENT DOCUMENTS

| | | |
|---|---|---|
| CA | 2918709 A1 | 1/2015 |
| WO | 2012084812 A1 | 6/2012 |
| WO | 2015012244 A1 | 1/2015 |

OTHER PUBLICATIONS

Patani et al (Chemical Reviews, vol. 96 (8) 1996 (Year: 1996).*
Int'l Preliminary Report on Patentability dated Sep. 11, 2018 in Int'l Application No. PCT/JP2017/009710.
Int'l Search Report dated May 22, 2017 Int'l Application No. PCT/JP2017/009710.

* cited by examiner

*Primary Examiner* — Savitha M Rao
(74) *Attorney, Agent, or Firm* — Panitch Schwarze Belisario & Nadel LLP

(57) ABSTRACT

A composition for controlling a plant disease is provided, containing a tetrazolinone compound represented by formula (1), wherein $X^1$ represents a halogen atom, a C1-C6 alkyl group, or a C1-C6 alkoxy group, and $X^2$ represents a C1-C3 alkyl group, a C3-C4 cycloalkyl group, a halogen atom, or a C1-C3 alkoxy group, and a carboxamide compound represented by formula (2). A method for controlling a plant disease is also provided, containing a step of applying an effective amount of the tetrazolinone compound represented by formula (1) and an effective amount of the carboxamide compound represented by formula (2) to a plant or soil for cultivating the plant. Both the composition and the method have excellent control efficacies against plant diseases.

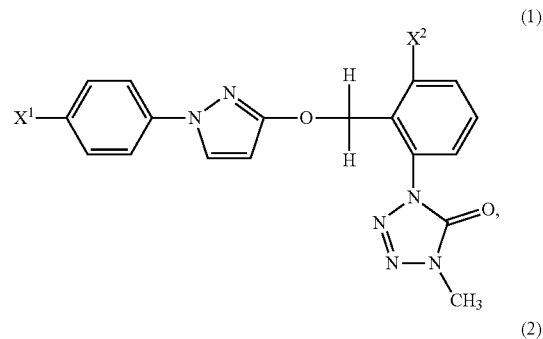

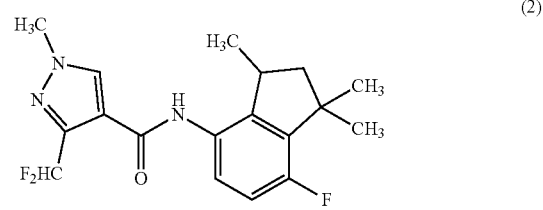

4 Claims, No Drawings

SYNERGISTIC FUNGICIDAL COMPOSITION FOR CONTROLLING PLANT DISEASES

CROSS-REFERENCE TO RELATED APPLICATION

This application is a Section 371 of International Application No. PCT/JP2017/009710, filed Mar. 10, 2017, which was published in the English language on Sep. 14, 2017, under International Publication No. WO 2017/155086 A1, which claims priority under 35 U.S.C. § 119 (b) to Japanese Application No. 2016-048171, filed Mar. 11, 2016, the disclosures of which are incorporated herein by reference in their entirety.

TECHNICAL FIELD

This application claims priority to and the benefit of Japanese Patent Application No. 2016-048171 filed on Mar. 11, 2016, the entire contents of which are incorporated herein by reference.

The present invention relates to a composition for controlling plant diseases and a method for controlling plant diseases.

BACKGROUND ART

Hitherto, some compounds have been known as an active ingredient for a composition for controlling plant diseases (see Patent Literatures 1 and 2).

CITATION LIST

Patent Literature

[PTL 1] WO 2015/012244 pamphlet
[PTL 2] WO 2012/084812 pamphlet

SUMMARY OF INVENTION

Technical Problem

An object of the present invention is to provide a composition for controlling plant diseases and a method for controlling plant diseases, each having an excellent control efficacy on plant diseases.

Solution to Problem

The present inventors have intensively studied to find out a composition for controlling plant diseases and a method for controlling plant diseases, each having an excellent control efficacy on plant diseases. As a result, they have found out that a composition comprising a tetrazolinone compound represented by the below-mentioned formula (1) and a carboxamide compound represented by the below-mentioned formula (2) shows an excellent control efficacy on plant diseases.

That is, the present invention provides the followings:

[1] A composition for controlling a plant disease comprising a tetrazolinone compound represented by formula (1):

[Chem. 1]

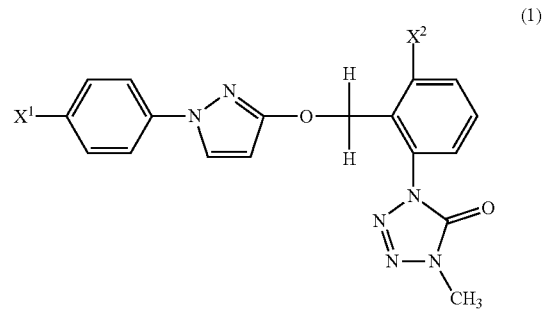

wherein
$X^1$ represents a halogen atom, a C1-C6 alkyl group, or a C1-C6 alkoxy group, and
$X^2$ represents a C1-C3 alkyl group, a C3-C4 cycloalkyl group, a halogen atom, or a C1-C3 alkoxy group, and
a carboxamide compound represented by formula (2):

[Chem. 2]

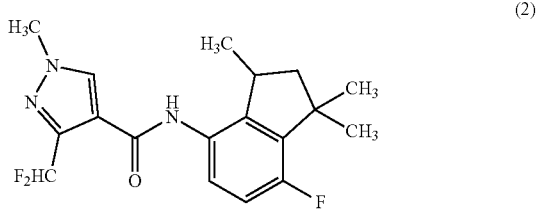 [SMILES: CC1CC(C)(C)c2c(F)ccc(NC(=O)c3cn(C)nc3C(F)F)c21]

[2] The composition for controlling a plant disease described in [1] wherein the tetrazolinone compound is the compound represented by formula (1) wherein $X^1$ represents a halogen atom or a C1-C6 alkyl group, and $X^2$ represents a C1-C3 alkyl group or a halogen atom.

[3] The composition for controlling a plant disease described in [1] wherein the tetrazolinone compound is the compound represented by formula (1) wherein $X^1$ represents a chlorine atom, a bromine atom, or a methoxy group, and $X^2$ represents a methyl group.

[4] The composition for controlling a plant disease described in [1] wherein the tetrazolinone compound is the compound represented by formula (1) wherein $X^1$ represents a chlorine atom, a bromine atom, or a methoxy group, and $X^2$ represents a chlorine atom.

[5] The composition for controlling a plant disease described in [1] wherein the tetrazolinone compound is the compound represented by formula (1) wherein $X^1$ represents a chlorine atom, and $X^2$ represents a methyl group.

[6] The composition for controlling a plant described in any one of [1] to [5] wherein a weight ratio of the tetrazolinone compound to the carboxamide compound is 1:0.0125 to 1:500.

[7] A method for controlling a plant disease, comprising a step of applying each effective amount of a tetrazolinone compound represented by formula (1):

[Chem. 3]

(1)

wherein

X¹ represents a halogen atom, a C1-C6 alkyl group, or a C1-C6 alkoxy group, and

X² represents a C1-C3 alkyl group, a C3-C4 cycloalkyl group, a halogen atom, or a C1-C3 alkoxy group, and a carboxamide compound represented by formula (2):

[Chem. 4]

(2)

to a plant or soil for cultivating the plant.

[8] A method for controlling a plant disease, comprising a step of applying each effective amount of a tetrazolinone compound represented by formula (1):

[Chem. 5]

(1)

wherein

X¹ represents a halogen atom, a C1-C6 alkyl group, or a C1-C6 alkoxy group, and

X² represents a C1-C3 alkyl group, a C3-C4 cycloalkyl group, a halogen atom, or a C1-C3 alkoxy group, and a carboxamide compound represented by formula (2):

[Chem. 6]

(2)

to a seed.

[9] A combined use of a tetrazolinone compound represented by formula (1):

[Chem. 7]

(1)

wherein

X¹ represents a halogen atom, a C1-C6 alkyl group, or a C1-C6 alkoxy group, and

X² represents a C1-C3 alkyl group, a C3-C4 cycloalkyl group, a halogen atom, or a C1-C3 alkoxy group, and a carboxamide compound represented by formula (2):

[Chem. 8]

(2)

The present invention can control plant diseases.

DESCRIPTION OF EMBODIMENTS

The composition for controlling plant diseases of the present invention (hereinafter, referred to as "present composition") comprises the above-mentioned tetrazolinone compound represented by formula (1) (hereinafter, referred to as "present compound 1") and the above-mentioned carboxamide compound represented by formula (2) (hereinafter, referred to as "present compound 2").

The substituent(s) as described herein is/are explained.

The expression of "C1-C3" as described herein represents that the number of the carbon atom is from 1 to 3.

The term of "halogen atom" as described herein represents a fluorine atom, a chlorine atom, a bromine atom, and an iodine atom.

The term of "C1-C6 alkyl group" as described herein represents a straight- or branched-chain saturated hydrocarbon group having 1 to 6 of carbon atom(s), and includes, for example, a methyl group, an ethyl group, a propyl group, an isopropyl group, a butyl group, an isobutyl group, a sec-butyl group, a tert-butyl group, a pentyl group, a neopentyl group, a hexyl group, and the like. Also, the term of "C1-C3 alkyl group" as described herein represents a straight- or branched-saturated hydrocarbon group having 1 to 3 of carbon atom(s), and includes, for example, a methyl group, an ethyl group, a propyl group, and an isopropyl group.

The term of "C1-C6 alkoxy group" as described herein represents the above-defined "C1-C6 alkyl group" attached to an oxygen atom, and includes, for example, a methoxy group, an ethoxy group, a propoxy group, a butoxy group, a pentyloxy group, and a hexyloxy group. The term of "C1-C3 alkoxy group" as described herein represents the above-defined "C1-C3 alkyl group" attached to an oxygen atom, and includes, for example, a methoxy group, an ethoxy group, and a propoxy group.

The term of "C3-C4 cycloalkyl group" as described herein represents a cyclic saturated hydrocarbon group having 3 to 4 of carbon atoms, and includes, for example, a cyclopropyl group and a cyclobutyl group.

First, the present compound 1 is described.

The present compound 1 is a compound described in, for example, WO 2015/012244 pamphlet, and can be prepared according to the process described therein.

Examples of the present compound 1 include the following compounds and the compounds shown in Table 1.

A compound represented by the formula (1) wherein $X^1$ represents a halogen atom or a C1-C6 alkyl group, and $X^2$ represents a C1-C3 alkyl group or a halogen atom.

A compound represented by the formula (1) wherein $X^1$ represents a chlorine atom, a bromine atom, or a methoxy group, and $X^2$ represents a methyl group.

A compound represented by the formula (1) wherein $X^1$ represents a chlorine atom, a bromine atom, or a methoxy group, and $X^2$ represents a chlorine atom.

A compound represented by the formula (1) wherein $X^1$ represents a chlorine atom, and $X^2$ represents a methyl group.

TABLE 1

| | Chemical Name |
|---|---|
| Present compound 1-1 | 1-(2-{[1-(4-chlorophenyl)-1H-pyrazol-3-yl]oxymethyl}-3-chlorophenyl)-4-methyl-1,4-dihydrotetrazol-5-one |
| Present compound 1-2 | 1-(2-{[1-(4-chlorophenyl)-1H-pyrazol-3-yl]oxymethyl}-3-bromophenyl)-4-methyl-1,4-dihydrotetrazol-5-one |
| Present compound 1-3 | 1-(2-{[1-(4-chlorophenyl)-1H-pyrazol-3-yl]oxymethyl}-3-methylphenyl)-4-methyl-1,4-dihydrotetrazol-5-one |
| Present compound 1-4 | 1-(2-{[1-(4-methoxyphenyl)-1H-pyrazol-3-yl]oxymethyl}-3-methylphenyl)-4-methyl-1,4-dihydrotetrazol-5-one |
| Present compound 1-5 | 1-(2-{[1-(4-chlorophenyl)-1H-pyrazol-3-yl]oxymethyl}-3-methoxyphenyl)-4-methyl-1,4-dihydrotetrazol-5-one |
| Present compound 1-6 | 1-(2-{[1-(4-chlorophenyl)-1H-pyrazol-3-yl]oxymethyl}-3-ethylphenyl)-4-methyl-1,4-dihydrotetrazol-5-one |
| Present compound 1-7 | 1-(2-{[1-(4-chlorophenyl)-1H-pyrazol-3-yl]oxymethyl}-3-cyclopropylphenyl)-4-methyl-1,4-dihydrotetrazol-5-one |
| Present compound 1-8 | 1-(2-{[1-(4-bromophenyl)-1H-pyrazol-3-yl]oxymethyl}-3-methylphenyl)-4-methyl-1,4-dihydrotetrazol-5-one |

Next, the present compound 2 is described.

The present compound 2 is a compound described in, for example, WO 2012/084812 pamphlet, and can be prepared according to the process described therein.

Here the present compound 2 includes enantiomers. Accordingly, the present compound 2 may include these isomers each singly, or any mixture composed of these isomers each in an arbitrary ratio of the respective isomer. Specific examples of optical active isomers that are included in the present compound 2 are shown in Table 2 below. Among them, the present compound 2-R shown in Table 2 is preferred.

TABLE 2

| | Chemical Name |
|---|---|
| Present compound 2-R | 3-Difluoromethyl-1-methyl-N-[(3R)-7-fluoro-1,1,3-trimethylindan-4-yl]pyrazole-4-carboxamide |
| Present compound 2-S | 3-Difluoromethyl-1-methyl-N-[(3S)-7-fluoro-1,1,3-trimethylindan-4-yl]pyrazole-4-carboxamide |

The weight ratio of the present compound 1 to the present compound 2 is within a range of usually 1:0.0125 to 1:500, preferably 1:0.025 to 1:100, and more preferably 1:0.1 to 1:10.

Although the present composition may be a mixture as itself of the present compound 1 and the present compound 2, the present composition is usually prepared by mixing the present compound 1, the present compound 2 and an inert carrier, and if necessary, adding a surfactant or other auxiliary agents for formulation, and then formulating into the form of oil solutions, emulsifiable concentrates, flowables, wettable powders, granulated wettable powders, dusts, granules and the others. Such formulations may be used by itself or with an addition of other inert components as an agent for controlling plant diseases.

The present composition may comprises usually 0.1 to 99% by weight, preferably 0.2 to 90% by weight, and more preferably 1 to 80% by weight of the present compound 1 and the present compound 2 in total.

Examples of an inert carrier used on formulating include a solid carrier and a liquid carrier, and examples of the solid carrier include finely-divided powders or particles consisting of minerals (for example, kaolin clay, attapulgite clay, bentonite, montmorillonite, acid clay, pyrophyllite, talc, diatomaceous earth, or calcite), natural organic substances (for example, corncob powder, or walnut shell powder), synthetic organic substances (for example, urea), salts (for example, calcium carbonate, or ammonium sulfate), synthetic inorganic substances (for example, synthetic hydrous silicon oxide) and so on. Also, examples of the liquid carrier include aromatic hydrocarbons (for example, xylene, alkyl benzene, or methylnaphthalene), alcohols (for example, 2-propanol, ethylene glycol, propylene glycol, or ethylene glycol monoethyl ether), ketones (for example, acetone, cyclohexanone, or isophorone), vegetable oils (for example, soybean oil, or cotton oils), petroleum-derived aliphatic hydrocarbons, esters, dimethyl sulfoxide, acetonitrile and water.

Examples of the surfactant include anionic surfactant (for example, alkyl sulfate salt, alkylaryl sulfonate salt, dialkyl sulfosuccinate salt, polyoxyethylene alkylaryl ether phosphates, lignin sulfonate, or naphthalene sulfonate formaldehyde polycondensation), nonionic surfactant (for example, polyoxyethylene alkylaryl ether, polyoxyethylene alkyl polyoxypropylene block copolymer, or sorbitan fatty acid ester) and cationic surfactant (for example, alkyltrimethyl ammonium salt).

Examples of the other auxiliary agents for formulation include water-soluble polymer (for example, polyvinyl alcohol, or polyvinyl pyrrolidone), polysaccharides (for example, arabic gum, alginic acid and salts thereof, CMC (carboxymethyl-cellulose), or xanthan gum), inorganic substances (for example, aluminum magnesium silicate, or alumina-sol), antiseptic agent, coloring agent, and PAP (isopropyl acid phosphate), and stabilizing agent (for example, BHT (2,6-di-tert-butyl-4-methylphenol)).

The present composition may also be prepared by separately formulating the present compound 1 and the present compound 2 into different formulations respectively according to the above-mentioned processes, if necessary, further diluting them with water, thereafter, mixing the separately prepared different formulations or the resultant dilute solutions thereof with each other.

The present composition may further comprise one or more other fungicide(s) and/or insecticide(s).

The present composition can be applied to a plant or soil for cultivating the plant to control the plant diseases.

Examples of the plant diseases which can be controlled by the present invention include the following diseases, but are not limited thereto.

Rice diseases: blast (*Magnaporthe grisea*), brown spot (*Cochliobolus miyabeanus*), sheath blight (*Rhizoctonia solani*), and bakanae disease (*Gibberella fujikuroi*);

Wheat diseases: powdery mildew (*Erysiphe graminis*), fusarium Head blight (*Fusarium graminearum, F. avenaceum, F. culmorum, Microdochium nivale*), rust (for example, yellow rust (*Puccinia striiformis*), black rust (*P. graminis*), Brown rust (*P. recondita*)), snow mold (*Microdochiumv nivale*), typhula snow blight (*Typhula* sp.), loose smut (*Ustilago tritici*), stinking smut (*Tilletia caries*), eyespot (*Pseudocercosporella herpotrichoides*), Septoria leaf blotch (*Mycosphaerella graminicola*), glume blotch (*Stagonospora nodorum*), and tan spot (*Pyrenophora triticirepenti*);

Barley diseases: powdery mildew (*Erysiphe graminis*), loose smut (*Fusarium graminearum, F. avenaceum, F. culmorum, Microdochium nivale*), rust (*Puccinia striiformis, P. graminis, P. hordei*), loose smut (*Ustilago nuda*), scald (*Rhynchosporium secalis*), net blotch (*Pyrenophora teres*), spot blotch (*Cochliobolus sativus*), leaf stripe (*Pyrenophora graminea*), and damping-off caused by rhizoctonia fungus (*Rhizoctonia solani*);

Corn diseases: smut (*Ustilago maydis*), southern leaf blight (*Cochliobolus heterostrophus*), zonate leaf spot (*Gloeocercospora sorghi*), southern rust (*Puccinia polysora*), gray leaf spot (*Cercospora zeae-maydis*), and damping-off caused by rhizoctonia fungus (*Rhizoctonia solani*);

Citrus diseases: melanose (*Diaporthe citri*), scab (*Elsinoe fawcetti*), fruit rot (*Penicillium digitatum, P. italicum*), and Phytophthora disease (*Phytophthora parasitica, Phytophthora citrophthora*);

Apple diseases: blossom blight (*Monilinia mali*), canker (*Valsa ceratosperma*), powdery mildew (*Podosphaera leucotricha*), Alternaria leaf spot (*Alternaria alternata* apple pathotype), scab (*Venturia inaequalis*), bitter rot (*Colletotrichum acutatum*), and crown rot (*Phytophthora cactorum*);

Pear diseases: scab (*Venturia nashicola, V. pirina*), black spot (*Alternaria alternata* Japanese pear pathotype), rust (*Gymnosporangium haraeanum*), phytophthora fruit rot, Phytophthora crown and root rot (*Phytophthora cactorum*), and brown spot (*Stemphilium vesicarium*);

Peach diseases: brown rot (*Monilinia fructicola*), scab (*Cladosporium carpophilum*), and Phomopsis rot (*Phomopsis* sp.);

Grapes diseases: anthracnose (*Elsinoe ampelina*), ripe rot (*Glomerella cingulata*), powdery mildew (*Uncinula necator*), rust (*Phakopsora ampelopsidis*), black rot (*Guignardia bidwellii*), and downy mildew (*Plasmopara viticola*);

Diseases of Japanese persimmon: anthracnose (*Gloeosporium kaki*), and leaf spot (*Cercospora kaki, Mycosphaerella nawae*);

Diseases of Cucurbitaceae: anthracnose (*Colletotrichum lagenarium*), powdery mildew (*Sphaerotheca fuliginea*), gummy stem blight (*Mycosphaerella melonis*), Fusarium wilt (*Fusarium oxysporum*), downy mildew (*Pseudoperonospora cubensis*), Phytophthora rot (*Phytophthora* sp.), and damping-off (*Pythium* sp.);

Tomato diseases: early blight (*Alternaria solani*), leaf mold (*Cladosporium fulvum*), and late blight (*Phytophthora infestans*);

Eggplant disease: brown spot (*Phomopsis vexans*), and powdery mildew (*Erysiphe cichoracearum*);

Diseases of brassica family: Alternaria leaf spot (*Alternaria japonica*), white spot (*Cercosporella brassicae*), clubroot (*Plasmodiophora brassicae*), and downy mildew (*Peronospora parasitica*);

Welsh onion diseases: rust (*Puccinia allii*), and downy mildew (*Peronospora destructor*);

Soybean diseases: purple stain (*Cercospora kikuchii*), Sphaceloma scad (*Elsinoe glycines*), pod and stem blight (*Diaporthe phaseolorum* var. *sojae*), septoria brown spot (*Septoria glycines*), Cercospora leaf spot (*Cercospora sojina*), rust (*Phakopsora pachyrhizi*), phytophthora root and stem rot (*Phytophthora sojae*), damping-off caused by rhizoctonia fungus (*Rhizoctonia solani*), target spot (*Corynespora casiicola*), and sclerotinia rot (*Sclerotinia sclerotiorum*);

Kidney bean diseases: anthracnose (*Colletotrichum lindemthianum*);

Peanut diseases: leaf spot (*Cercospora personata*), brown leaf spot (*Cercospora arachidicola*), and southern blight (*Sclerotium rolfsii*);

Garden pea diseases: powdery mildew (*Erysiphe pisi*);

Potato diseases: early blight (*Alternaria solani*), late blight (*Phytophthora infestans*), pink rot (*Phytophthora erythroseptica*), and powdery scab (*Spongospora subterranean f.* sp. *subterranea*);

Strawberry diseases: powdery mildew (*Sphaerotheca humuli*), and anthracnose (*Glomerella cingulata*);

Tea diseases: net blister blight (*Exobasidium reticulatum*), white scab (*Elsinoe leucospila*), gray blight (*Pestalotiopsis* sp.), and anthracnose (*Colletotrichum theaesinensis*);

Tabacco diseases: brown spot (*Alternaria longipes*), powdery mildew (*Erysiphe cichoracearum*), anthracnose (*Colletotrichum tabacum*), downy mildew (*Peronospora tabacina*), and black shank (*Phytophthora nicotianae*);

Rape seed diseases: sclerotinia rot (*Sclerotinia sclerotiorum*), and rape seed damping-off caused by *Rhizoctonia solani* (*Rhizoctonia solani*);

Cotton diseases: cotton damping-off caused by *Rhizoctonia solani* (*Rhizoctonia solani*);

Sugar beet diseases: cercospora leaf spot (*Cercospora beticola*), leaf blight (*Thanatephorus cucumeris*), root rot (*Thanatephorus cucumeris*), and aphanomyces root rot (*Aphanomyces cochlioides*);

Rose diseases: blackspot (*Diplocarpon rosae*), powdery mildew (*Sphaerotheca pannosa*), and downy mildew (*Peronospora sparsa*);

Chrysanthemum and Asteraceae vegetable diseases: downy mildew (*Bremia lactucae*), leaf blight (*Septoria chrysanthemi-indici*), and white rust (*Puccinia horiana*);

Various plants diseases: diseases caused by *Pythium* spp. (*Pythium aphanidermatum, Pythium debarianum, Pythium graminicola, Pythium irregulare, Pythium ultimum*), Gray mold (*Botrytis cinerea*), and Sclerotinia rot (*Sclerotinia sclerotiorum*);

Japanese radish diseases: Alternaria leaf spot (*Alternaria brassicicola*);

Turfgrass diseases: dollar spot (*Sclerotinia homeocarpa*), brown patch, and large patch (*Rhizoctonia solani*);

Banana diseases: Sigatoka disease (*Mycosphaerella fijiensis, Mycosphaerella musicola*);

Sunflower diseases: downy mildew (*Plasmopara halstedii*);

Seed diseases or diseases in the early stages of the growth of various plants caused by bacteria of *Aspergillus* spp., *Penicillium* spp., *Fusarium* spp., *Gibberella* spp., *Tricoderma* spp., *Thielaviopsis* spp., *Rhizopus* spp., *Mucor* spp., *Corticium* spp., *Phoma* spp., *Rhizoctonia* spp., *Diplodia* spp.; and Viral diseases of various plants mediated by *Polymixa* spp. or *Olpidium* spp.

Examples of the plants to which the present composition can be applied include the followings, but are not limited thereto.

Crops: corn, rice, wheat, barley, rye, oat, sorghum, cotton, soybean, adzuki bean, kidney bean, peanut, buckwheat, beet, rapeseed, sunflower, sugar cane, tobacco, and the others;

Vegetables: solanaceous vegetables (for example, eggplant, tomato, pimento, pepper, or potato), cucurbitaceous vegetables (for example, cucumber, pumpkin, zucchini, water melon, melon, or squash), cruciferous vegetables (for example, Japanese radish, white turnip, horseradish, kohlrabi, Chinese cabbage, cabbage, leaf mustard, broccoli, or cauliflower), asteraceous vegetables (for example, burdock, crown daisy, artichoke, or lettuce), liliaceous vegetables (for example, welsh onion, onion, garlic, or asparagus), ammiaceous vegetables (for example, carrot, parsley, celery, or parsnip), chenopodiaceous vegetables (for example, spinach, or Swiss chard), lamiaceous vegetables (for example, perilla, mint, or basil), strawberry, sweet potato, glutinous yam, eddoe, and the others;

Flowers;

Foliage plants;

Turfgrass;

Fruits: pomaceous fruits (for example, apple, pear, Japanese pear, Chinese quince, or quince), stone fleshy fruits (for example, peach, plum, nectarine, Japanese apricot (*Prunus mume*), cherry fruit, apricot, or prune), citrus fruits (for example, Citrus unshiu, orange, lemon, lime, or grapefruit), nuts (for example, chestnuts, walnuts, hazelnuts, almond, pistachio, cashew nuts, or macadamia nuts), berry fruits (for example, blueberry, cranberry, blackberry, or raspberry), grapes, Japanese persimmon, olive, Japanese plum, banana, coffee, date palm, coconuts, and the others; and Trees other than fruit trees: tea, mulberry, flowering plants, roadside trees (for example, ash, birch, dogwood, eucalyptus, ginkgo (*Ginkgo biloba*), lilac, maple, oak (*quercus*), poplar, Judas tree, Formosan gum (*Liquidambar formosana*), plane tree, zelkova, Japanese arborvitae (*Thuja standishii*), fir wood, hemlock, juniper, pinus, picea, or yew (*Taxus cuspidate*)), and the others.

The above-mentioned "plant(s)" may include plant(s) whose resistance has been imparted by genetic recombination.

Exemplary embodiments of the present composition include the followings, but are not limited thereto.

A present composition wherein the combination of the present compound 1 and the present compound 2 represents as follows:

A combination of the present compound 1-1 and the present compound 2;

A combination of the present compound 1-1 and the present compound 2-R;

A combination of the present compound 1-1 and the present compound 2-S;

A combination of the present compound 1-2 and the present compound 2;

A combination of the present compound 1-2 and the present compound 2-R;

A combination of the present compound 1-2 and the present compound 2-S;

A combination of the present compound 1-3 and the present compound 2;

A combination of the present compound 1-3 and the present compound 2-R;

A combination of the present compound 1-3 and the present compound 2-S;

A combination of the present compound 1-4 and the present compound 2;

A combination of the present compound 1-4 and the present compound 2-R;

A combination of the present compound 1-4 and the present compound 2-S;

A combination of the present compound 1-5 and the present compound 2;

A combination of the present compound 1-5 and the present compound 2-R;

A combination of the present compound 1-5 and the present compound 2-S;

A combination of the present compound 1-6 and the present compound 2;

A combination of the present compound 1-6 and the present compound 2-R;

A combination of the present compound 1-6 and the present compound 2-S;

A combination of the present compound 1-7 and the present compound 2;

A combination of the present compound 1-7 and the present compound 2-R;

A combination of the present compound 1-7 and the present compound 2-S;

A combination of the present compound 1-8 and the present compound 2;

A combination of the present compound 1-8 and the present compound 2-R; and

A combination of the present compound 1-8 and the present compound 2-S.

A present composition comprising the present compound 1-1 and any one of the present compound 2, the present compound 2-R or the present compound 2-S wherein the weight ratio of the present compound 1-1 to any one of the present compound 2, the present compound 2-R or the present compound 2-S is 1:0.0125 to 1:500;

A present composition comprising the present compound 1-1 and any one of the present compound 2, the present compound 2-R or the present compound 2-S wherein the weight ratio of the present compound 1-1 to any one of the present compound 2, the present compound 2-R or the present compound 2-S is 1:0.025 to 1:100;

A present composition comprising the present compound 1-1 and any one of the present compound 2, the present compound 2-R or the present compound 2-S wherein the weight ratio of the present compound 1-1 to any one of the present compound 2, the present compound 2-R or the present compound 2-S is 1:0.1 to 1:10;

A present composition comprising the present compound 1-2 and any one of the present compound 2, the present compound 2-R or the present compound 2-S wherein the weight ratio of the present compound 1-2 to any one of the present compound 2, the present compound 2-R or the present compound 2-S is 1:0.0125 to 1:500;

A present composition comprising the present compound 1-2 and any one of the present compound 2, the present compound 2-R or the present compound 2-S wherein the weight ratio of the present compound 1-2 to any one of the present compound 2, the present compound 2-R or the present compound 2-S is 1:0.025 to 1:100;

A present composition comprising the present compound 1-2 and any one of the present compound 2, the present compound 2-R or the present compound 2-S wherein the weight ratio of the present compound 1-2 to any one of the present compound 2, the present compound 2-R or the present compound 2-S is 1:0.1 to 1:10;

A present composition comprising the present compound 1-3 and any one of the present compound 2, the present compound 2-R or the present compound 2-S wherein the weight ratio of the present compound 1-3 to any one of the present compound 2, the present compound 2-R or the present compound 2-S is 1:0.0125 to 1:500;

A present composition comprising the present compound 1-3 and any one of the present compound 2, the present compound 2-R or the present compound 2-S wherein the weight ratio of the present compound 1-3 to any one of the present compound 2, the present compound 2-R or the present compound 2-S is 1:0.025 to 1:100;

A present composition comprising the present compound 1-3 and any one of the present compound 2, the present compound 2-R or the present compound 2-S wherein the weight ratio of the present compound 1-3 to any one of the present compound 2, the present compound 2-R or the present compound 2-S is 1:0.1 to 1:10;

A present composition comprising the present compound 1-4 and any one of the present compound 2, the present compound 2-R or the present compound 2-S wherein the weight ratio of the present compound 1-4 to any one of the present compound 2, the present compound 2-R or the present compound 2-S is 1:0.0125 to 1:500;

A present composition comprising the present compound 1-4 and any one of the present compound 2, the present compound 2-R or the present compound 2-S wherein the weight ratio of the present compound 1-4 to any one of the present compound 2, the present compound 2-R or the present compound 2-S is 1:0.025 to 1:100;

A present composition comprising the present compound 1-4 and any one of the present compound 2, the present compound 2-R or the present compound 2-S wherein the weight ratio of the present compound 1-4 to any one of the present compound 2, the present compound 2-R or the present compound 2-S is 1:0.1 to 1:10;

A present composition comprising the present compound 1-5 and any one of the present compound 2, the present compound 2-R or the present compound 2-S wherein the weight ratio of the present compound 1-5 to any one of the present compound 2, the present compound 2-R or the present compound 2-S is 1:0.0125 to 1:500;

A present composition comprising the present compound 1-5 and any one of the present compound 2, the present compound 2-R or the present compound 2-S wherein the weight ratio of the present compound 1-5 to any one of the present compound 2, the present compound 2-R or the present compound 2-S is 1:0.025 to 1:100;

A present composition comprising the present compound 1-5 and any one of the present compound 2, the present compound 2-R or the present compound 2-S wherein the weight ratio of the present compound 1-5 to any one of the present compound 2, the present compound 2-R or the present compound 2-S is 1:0.1 to 1:10;

A present composition comprising the present compound 1-6 and any one of the present compound 2, the present compound 2-R or the present compound 2-S wherein the weight ratio of the present compound 1-6 to any one of the present compound 2, the present compound 2-R or the present compound 2-S is 1:0.0125 to 1:500;

A present composition comprising the present compound 1-6 and any one of the present compound 2, the present compound 2-R or the present compound 2-S wherein the weight ratio of the present compound 1-6 to any one of the present compound 2, the present compound 2-R or the present compound 2-S is 1:0.025 to 1:100;

A present composition comprising the present compound 1-6 and any one of the present compound 2, the present compound 2-R or the present compound 2-S wherein the weight ratio of the present compound 1-6 to any one of the present compound 2, the present compound 2-R or the present compound 2-S is 1:0.1 to 1:10;

A present composition comprising the present compound 1-7 and any one of the present compound 2, the present compound 2-R or the present compound 2-S wherein the weight ratio of the present compound 1-7 to any one of the present compound 2, the present compound 2-R or the present compound 2-S is 1:0.0125 to 1:500;

A present composition comprising the present compound 1-7 and any one of the present compound 2, the present compound 2-R or the present compound 2-S wherein the weight ratio of the present compound 1-7 to any one of the present compound 2, the present compound 2-R or the present compound 2-S is 1:0.025 to 1:100;

A present composition comprising the present compound 1-7 and any one of the present compound 2, the present compound 2-R or the present compound 2-S wherein the weight ratio of the present compound 1-7 to any one of the present compound 2, the present compound 2-R or the present compound 2-S is 1:0.1 to 1:10;

A present composition comprising the present compound 1-8 and any one of the present compound 2, the present compound 2-R or the present compound 2-S wherein the weight ratio of the present compound 1-8 to any one of the present compound 2, the present compound 2-R or the present compound 2-S is 1:0.0125 to 1:500;

A present composition comprising the present compound 1-8 and any one of the present compound 2, the present compound 2-R or the present compound 2-S wherein the weight ratio of the present compound 1-8 to any one of the present compound 2, the present compound 2-R or the present compound 2-S is 1:0.025 to 1:100; and A present composition comprising the present compound 1-8 and any one of the present compound 2, the present compound 2-R or the present compound 2-S wherein the weight ratio of the present compound 1-8 to any one of the present compound 2, the present compound 2-R or the present compound 2-S is 1:0.1 to 1:10.

The method for controlling plant diseases of the present invention (hereinafter, referred to as "control method of the present invention") is carried out by applying each of an effective amount of the present compound 1 and the present compound 2 to a plant or soil for cultivating the plant. Examples of the plant include foliage of a plant, seeds of a plant and bulbs of a plant. Moreover, the bulbs described herein mean discoid stems, corms, rhizomes, tubers, tuberous, and tuberous roots.

In the control method of the present invention, the present compound 1 and the present compound 2 may be applied separately to a plant or soil for cultivating the plant in the same period, but are usually applied as the present composition in terms of a convenience on applying.

In the control method of the present invention, examples of the method of applying the present compound 1 and the present compound 2 include foliage treatment, soil treatment, root treatment, and seed treatment.

Such the foliage treatment includes, for example, a method of applying the present compound 1 and the present compound 2 onto surface of a plant to be cultivated by a foliar application or a stem application.

Such the soil treatment includes, for example, soil broadcast, soil incorporation, and irrigation of the agent solution comprising the present compound 1 and the present compound 2 to a soil.

Such the root treatment includes, for example, a method of soaking a whole or a root of the plant into a medicinal solution comprising the present compound 1 and the present compound 2, and a method of attaching a solid formulation comprising the present compound 1, the present compound 2 and the solid carrier to a root of the plant.

Such the seed treatment includes, for example, an applying of the present composition to a seed or a bulb of the plant to be prevented from the plant disease, specifically, for example, spray treatment by spraying a suspension of the present composition in a mist form onto the surface of a seed or the surface of a bulb, smear treatment by applying the wettable powders, the emulsifiable concentrates or the flowables of the present composition with added by small amounts of water or as itself to a seed or a bulb, immersion treatment by immersing a seed into a solution of the present composition for a certain period of time, film-coating treatment and pellet-coating treatment.

Each dose of the present compound 1 and the present compound 2 in the control method of the present invention may be varied depending on a kind of plant to be applied, a kind or a frequency of an occurrence of a plant disease as a control subject, a dosage form, an application period, an application method, an application site, a climate condition, and the like. In case of an application to a foliage of the plant or soil for cultivating the plant, a total amount of the present compound 1 and the present compound 2 is within the range of usually 1 to 500 g, preferably 2 to 200 g, and more preferably 10 to 100 g, per 1000 $m^2$. Also a total amount of the present compound 1 and the present compound 2 in the treatment for seed is within the range of usually 0.001 to 10 g, and preferably 0.01 to 1 g, per 1 kg of seeds.

The emulsifiable concentrates, the wettable powders or the flowables, etc., are usually applied by diluting them with water, and then spreading them. In this case, each concentration of the present compound 1 and the present compound 2 contains usually 0.0005 to 2% by weight, and preferably 0.005 to 1% by weight of the present compound 1 and the present compound 2 in total. The dusts or the granules, etc., are usually applied as itself without diluting them.

EXAMPLES

The present invention is described in more detail below by Formulation Examples and Test Examples, but the present invention should not be limited thereto.

First, Formulation Examples are described. Herein, "parts" means "parts by weight".

Formulation Example 1

Five (5) parts of any one of the present compound 2, the present compound 2-R or the present compound 2-S, 5 parts of the present compound 1-1, 35 parts of a mixture of white carbon and polyoxyethylene alkyl ether sulfate ammonium salt (weight ratio 1:1), and 55 parts of water are mixed, and the resultant solution is then subjected to fine grinding according to a wet grinding method to obtain each flowable.

Formulation Example 2

Five (5) parts of any one of the present compound 2, the present compound 2-R or the present compound 2-S, 5 parts of the present compound 1-2, 35 parts of a mixture of white carbon and polyoxyethylene alkyl ether sulfate ammonium salt (weight ratio 1:1), and 55 parts of water are mixed, and the resultant solution is then subjected to fine grinding according to a wet grinding method to obtain each flowable.

Formulation Example 3

Five (5) parts of any one of the present compound 2, the present compound 2-R or the present compound 2-S, 5 parts of the present compound 1-3, 35 parts of a mixture of white carbon and polyoxyethylene alkyl ether sulfate ammonium salt (weight ratio 1:1), and 55 parts of water are mixed, and the resultant solution is then subjected to fine grinding according to a wet grinding method to obtain each flowable.

Formulation Example 4

Five (5) parts of any one of the present compound 2, the present compound 2-R or the present compound 2-S, 5 parts of the present compound 1-4, 35 parts of a mixture of white carbon and polyoxyethylene alkyl ether sulfate ammonium salt (weight ratio 1:1), and 55 parts of water are mixed, and the resultant solution is then subjected to fine grinding according to a wet grinding method to obtain each flowable.

Formulation Example 5

Five (5) parts of any one of the present compound 2, the present compound 2-R or the present compound 2-S, 5 parts of the present compound 1-5, 35 parts of a mixture of white carbon and polyoxyethylene alkyl ether sulfate ammonium salt (weight ratio 1:1), and 55 parts of water are mixed, and the resultant solution is then subjected to fine grinding according to a wet grinding method to obtain each flowable.

Formulation Example 6

Five (5) parts of any one of the present compound 2, the present compound 2-R or the present compound 2-S, 5 parts of the present compound 1-6, 35 parts of a mixture of white carbon and polyoxyethylene alkyl ether sulfate ammonium salt (weight ratio 1:1), and 55 parts of water are mixed, and the resultant solution is then subjected to fine grinding according to a wet grinding method to obtain each flowable.

Formulation Example 7

Five (5) parts of any one of the present compound 2, the present compound 2-R or the present compound 2-S, 5 parts of the present compound 1-7, 35 parts of a mixture of white carbon and polyoxyethylene alkyl ether sulfate ammonium salt (weight ratio 1:1), and 55 parts of water are mixed, and the resultant solution is then subjected to fine grinding according to a wet grinding method to obtain each flowable.

Formulation Example 8

Five (5) parts of any one of the present compound 2, the present compound 2-R or the present compound 2-S, 5 parts of the present compound 1-8, 35 parts of a mixture of white carbon and polyoxyethylene alkyl ether sulfate ammonium salt (weight ratio 1:1), and 55 parts of water are mixed, and the resultant solution is then subjected to fine grinding according to a wet grinding method to obtain each flowable.

Formulation Example 9

Five (5) parts of any one of the present compound 2, the present compound 2-R or the present compound 2-S, 10 parts of the present compound 1-1, 1.5 parts of sorbitan trioleate, and 28 parts of aqueous solution that contained 2 parts of polyvinyl alcohol are mixed, and the resultant solution is then subjected to fine grinding according to a wet grinding method, and thereto are added 45.50 parts of an aqueous solution that contained 0.05 parts of xanthan gum and 0.1 part of aluminum magnesium silicate, followed by adding 10 parts of propylene glycol, and the mixture is blended by stiffing to obtain each flowable.

Formulation Example 10

Five (5) parts of any one of the present compound 2, the present compound 2-R or the present compound 2-S, 10 parts of the present compound 1-2, 1.5 parts of sorbitan trioleate, and 28 parts of aqueous solution that contained 2 parts of polyvinyl alcohol are mixed, and the resultant solution is then subjected to fine grinding according to a wet grinding method, and thereto are added 45.50 parts of an aqueous solution that contained 0.05 parts of xanthan gum and 0.1 part of aluminum magnesium silicate, followed by adding 10 parts of propylene glycol, and the mixture is blended by stiffing to obtain each flowable.

Formulation Example 11

Five (5) parts of any one of the present compound 2, the present compound 2-R or the present compound 2-S, 10 parts of the present compound 1-3, 1.5 parts of sorbitan trioleate, and 28 parts of aqueous solution that contained 2 parts of polyvinyl alcohol are mixed, and the resultant solution is then subjected to fine grinding according to a wet grinding method, and thereto are added 45.50 parts of an aqueous solution that contained 0.05 parts of xanthan gum and 0.1 part of aluminum magnesium silicate, followed by adding 10 parts of propylene glycol, and the mixture is blended by stiffing to obtain each flowable.

Formulation Example 12

Five (5) parts of any one of the present compound 2, the present compound 2-R or the present compound 2-S, 10 parts of the present compound 1-4, 1.5 parts of sorbitan trioleate, and 28 parts of aqueous solution that contained 2 parts of polyvinyl alcohol are mixed, and the resultant solution is then subjected to fine grinding according to a wet grinding method, and thereto are added 45.50 parts of an aqueous solution that contained 0.05 parts of xanthan gum and 0.1 part of aluminum magnesium silicate, followed by adding 10 parts of propylene glycol, and the mixture is blended by stiffing to obtain each flowable.

Formulation Example 13

Five (5) parts of any one of the present compound 2, the present compound 2-R or the present compound 2-S, 10 parts of the present compound 1-5, 1.5 parts of sorbitan trioleate, and 28 parts of aqueous solution that contained 2 parts of polyvinyl alcohol are mixed, and the resultant solution is then subjected to fine grinding according to a wet grinding method, and thereto are added 45.50 parts of an aqueous solution that contained 0.05 parts of xanthan gum and 0.1 part of aluminum magnesium silicate, followed by adding 10 parts of propylene glycol, and the mixture is blended by stiffing to obtain each flowable.

Formulation Example 14

Five (5) parts of any one of the present compound 2, the present compound 2-R or the present compound 2-S, 10 parts of the present compound 1-6, 1.5 parts of sorbitan trioleate, and 28 parts of aqueous solution that contained 2 parts of polyvinyl alcohol are mixed, and the resultant solution is then subjected to fine grinding according to a wet grinding method, and thereto are added 45.50 parts of an aqueous solution that contained 0.05 parts of xanthan gum and 0.1 part of aluminum magnesium silicate, followed by adding 10 parts of propylene glycol, and the mixture is blended by stiffing to obtain each flowable.

Formulation Example 15

Five (5) parts of any one of the present compound 2, the present compound 2-R or the present compound 2-S, 10 parts of the present compound 1-7, 1.5 parts of sorbitan trioleate, and 28 parts of aqueous solution that contained 2 parts of polyvinyl alcohol are mixed, and the resultant solution is then subjected to fine grinding according to a wet grinding method, and thereto are added 45.50 parts of an aqueous solution that contained 0.05 parts of xanthan gum and 0.1 part of aluminum magnesium silicate, followed by adding 10 parts of propylene glycol, and the mixture is blended by stiffing to obtain each flowable.

Formulation Example 16

Five (5) parts of any one of the present compound 2, the present compound 2-R or the present compound 2-S, 10 parts of the present compound 1-8, 1.5 parts of sorbitan trioleate, and 28 parts of aqueous solution that contained 2 parts of polyvinyl alcohol are mixed, and the resultant solution is then subjected to fine grinding according to a wet grinding method, and thereto are added 45.50 parts of an aqueous solution that contained 0.05 parts of xanthan gum and 0.1 part of aluminum magnesium silicate, followed by adding 10 parts of propylene glycol, and the mixture is blended by stiffing to obtain each flowable.

Formulation Example 17

Forty (40) parts of any one of the present compound 2, the present compound 2-R or the present compound 2-S, 10 parts of the present compound 1-1, 3 parts of calcium lignosulfonate, 2 parts of sodium lauryl sulfate and 45 parts of synthetic hydrous silicon oxide are fully ground and mixed to obtain each wettable powder.

Formulation Example 18

Forty (40) parts of any one of the present compound 2, the present compound 2-R or the present compound 2-S, 10 parts of the present compound 1-2, 3 parts of calcium lignosulfonate, 2 parts of sodium lauryl sulfate and 45 parts of synthetic hydrous silicon oxide are fully ground and mixed to obtain each wettable powder.

Formulation Example 19

Forty (40) parts of any one of the present compound 2, the present compound 2-R or the present compound 2-S, 10 parts of the present compound 1-3, 3 parts of calcium lignosulfonate, 2 parts of sodium lauryl sulfate and 45 parts of synthetic hydrous silicon oxide are fully ground and mixed to obtain each wettable powder.

Formulation Example 20

Forty (40) parts of any one of the present compound 2, the present compound 2-R or the present compound 2-S, 10 parts of the present compound 1-4, 3 parts of calcium lignosulfonate, 2 parts of sodium lauryl sulfate and 45 parts of synthetic hydrous silicon oxide are fully ground and mixed to obtain each wettable powder.

Formulation Example 21

Forty (40) parts of any one of the present compound 2, the present compound 2-R or the present compound 2-S, 10 parts of the present compound 1-5, 3 parts of calcium lignosulfonate, 2 parts of sodium lauryl sulfate and 45 parts of synthetic hydrous silicon oxide are fully ground and mixed to obtain each wettable powder.

Formulation Example 22

Forty (40) parts of any one of the present compound 2, the present compound 2-R or the present compound 2-S, 10 parts of the present compound 1-6, 3 parts of calcium lignosulfonate, 2 parts of sodium lauryl sulfate and 45 parts of synthetic hydrous silicon oxide are fully ground and mixed to obtain each wettable powder.

Formulation Example 23

Forty (40) parts of any one of the present compound 2, the present compound 2-R or the present compound 2-S, 10 parts of the present compound 1-7, 3 parts of calcium lignosulfonate, 2 parts of sodium lauryl sulfate and 45 parts of synthetic hydrous silicon oxide are fully ground and mixed to obtain each wettable powder.

Formulation Example 24

Forty (40) parts of any one of the present compound 2, the present compound 2-R or the present compound 2-S, 10 parts of the present compound 1-8, 3 parts of calcium lignosulfonate, 2 parts of sodium lauryl sulfate and 45 parts of synthetic hydrous silicon oxide are fully ground and mixed to obtain each wettable powder.

Formulation Example 25

Five (5) parts of any one of the present compound 2, the present compound 2-R or the present compound 2-S, 5 parts of the present compound 1-1, 14 parts of polyoxyethylene styryl phenyl ether, 6 parts of dodecylbenzene sulfonic acid calcium salt, and 70 parts of xylene are mixed fully to obtain each formulation.

Formulation Example 26

Five (5) parts of any one of the present compound 2, the present compound 2-R or the present compound 2-S, 5 parts of the present compound 1-2, 14 parts of polyoxyethylene styryl phenyl ether, 6 parts of dodecylbenzene sulfonic acid calcium salt, and 70 parts of xylene are mixed fully to obtain each formulation.

Formulation Example 27

Five (5) parts of any one of the present compound 2, the present compound 2-R or the present compound 2-S, 5 parts of the present compound 1-3, 14 parts of polyoxyethylene styryl phenyl ether, 6 parts of dodecylbenzene sulfonic acid calcium salt, and 70 parts of xylene are mixed fully to obtain each formulation.

Formulation Example 28

Five (5) parts of any one of the present compound 2, the present compound 2-R or the present compound 2-S, 5 parts of the present compound 1-4, 14 parts of polyoxyethylene styryl phenyl ether, 6 parts of dodecylbenzene sulfonic acid calcium salt, and 70 parts of xylene are mixed fully to obtain each formulation.

Formulation Example 29

Five (5) parts of any one of the present compound 2, the present compound 2-R or the present compound 2-S, 5 parts of the present compound 1-5, 14 parts of polyoxyethylene styryl phenyl ether, 6 parts of dodecylbenzene sulfonic acid calcium salt, and 70 parts of xylene are mixed fully to obtain each formulation.

Formulation Example 30

Five (5) parts of any one of the present compound 2, the present compound 2-R or the present compound 2-S, 5 parts of the present compound 1-6, 14 parts of polyoxyethylene styryl phenyl ether, 6 parts of dodecylbenzene sulfonic acid calcium salt, and 70 parts of xylene are mixed fully to obtain each formulation.

Formulation Example 31

Five (5) parts of any one of the present compound 2, the present compound 2-R or the present compound 2-S, 5 parts of the present compound 1-7, 14 parts of polyoxyethylene styryl phenyl ether, 6 parts of dodecylbenzene sulfonic acid calcium salt, and 70 parts of xylene are mixed fully to obtain each formulation.

Formulation Example 32

Five (5) parts of any one of the present compound 2, the present compound 2-R or the present compound 2-S, 5 parts of the present compound 1-8, 14 parts of polyoxyethylene styryl phenyl ether, 6 parts of dodecylbenzene sulfonic acid calcium salt, and 70 parts of xylene are mixed fully to obtain each formulation.

Next, Test Examples are described.

Test Example 1

Any one of the present compounds 1-1 to 1-8, and any one of the present compound 2, the present compound 2-R or the present compound 2-S are mixed, and each of the resultant mixtures is diluted with dimethyl sulfoxide such that each concentration of the present compound 1, etc., and the present compound 2, etc., is 10 ppm. The resultant dilute solution is dispensed into a microtiter plate (with 96 wells) in 1 μl portion thereof per well. Thereto is then dispensed 150 μl of a potato dextrose broth medium (PDB medium) to which conidia of Septoria leaf blotch (*Mycosphaerella graminicola*) is inoculated in advance. This plate is cultured at 18° C. for four days, thereby allowing Septoria leaf blotch to undergo proliferation, and the absorbance at 550 nm of each well of the microtiter plate is then measured to examine a degree of growth of the Septoria leaf blotch.

The efficacy is calculated on the basis of the obtained degree of growth of the treated group and the untreated group, respectively, by the following "Equation 1". From the test results, a high efficacy is acknowledged.

$$\text{Efficacy}=100\times(X-Y)/X \qquad \text{Equation 1}$$

X: Degree of growth of fungus in the untreated group
Y: Degree of growth of fungus in the treated group

Test Example 2

A plastic pot is filled with soil and thereto wheat (cultivar. *Shirogane*) is seeded and the plants are grown in a greenhouse for ten days. Any one of the present compounds 1-1 to 1-8, and any one of the present compound 2, the present compound 2-R or the present compound 2-S are made to a formulation according to a method described in any one of the above-mentioned Formulation Examples 1 to 32, and each of the resultant formulation is diluted with water such that each concentration of the present compound 1, etc., and the present compound 2, etc., respectively is 100 ppm. The resultant dilute solution is sprayed to foliar parts so as to adhere adequately onto the surfaces of leaves of the above wheats. After spraying the dilute solution, the plants are air-dried, and one day after the application, an aqueous suspension of uredospores of Brown rust (*Puccinia recondita*) is inoculated by spraying thereto. After the inoculation, the plants are placed at 27° C. under humid condition for one day, and are then cultivated under lighting for ten to fifteen days, and a lesion area is examined (hereinafter referred to as "treated group").

Whereas, wheats are cultivated similarly to the treated group except that no foliage application of the above-mentioned agent solutions are done (hereinafter referred to as "untreated group"). A lesion area of Brown rust is examined similarly to the above-mentioned treated group.

From each of the lesion area of the treated group and the untreated group respectively, the efficacy of the treated group is calculated by the following Equation 2.

$$\text{Efficacy}=[1-(\text{lesion area of the treated group})/(\text{lesion area of the untreated group})]\times 100 \qquad \text{Equation 2}$$

Test Example 3

Each of the present compound 1-3 or the present compound 2 was dissolved into dimethyl sulfoxide such that each concentration of these compounds was adjusted to one hundred fifty times as much as the concentration indicated in the below-mentioned Table 3. The resultant agent solution was dispensed into each microtiter plate (with 96 wells) in 1 μl portion thereof per well. 149 μl of YBG medium to which conidia of Septoria leaf blotch (*Mycosphaerella graminicola*) was inoculated in advance (which was prepared by dissolving 10 g of yeast extract, 10 g of Bacto Peptone, and 20 mL of glycerol into 1 L of water, followed by sterilizing the medium) was dispensed into each of the well to which the agent solution was dispensed. The plate was cultivated at 18° C. for four days, thereby allowing Septoria leaf blotch (*Mycosphaerella graminicola*) to undergo proliferation, and the absorbance at 550 nm of each well of the microtiter plate was then measured to examine a degree of growth of Septoria leaf blotch (hereinafter referred to as "treated group").

Whereas, Septoria leaf blotch was proliferated similarly to the case of the treated group except that dimethyl sulfoxide was used instead of the agent solution, and the degree of the growth was examined (hereinafter referred to as "untreated group"). The efficacy was calculated from each of the obtained degree of growth of the treated group and the untreated group respectively by the following "Equation 1".

From the test results, it was acknowledged that a synergistic effect was shown in the mixed-use group of the present compound 1-3 and the present compound 2 in comparison with the case of each of the single-use group of the above-mentioned compounds respectively.

$$\text{Efficacy (\%)}=100\times(X-Y)/X \qquad \text{Equation 1}$$

X: Degree of growth of fungus in the untreated group
Y: Degree of growth of fungus in the treated group

TABLE 3

| Testing compound | Concentration in medium (ppm) | Mixing ratio (Present compound 1-3:Present compound 2) | Efficacy (%) |
|---|---|---|---|
| Present compound 1-3 | 0.01 | — | 37 |
| Present compound 1-3 | 0.0001 | — | 20 |
| Present compound 2 | 0.001 | — | 20 |
| Present compound 1-3 + Present compound 2 | 0.01 + 0.001 | 1:0.1 | 89 |
| Present compound 1-3 + Present compound 2 | 0.0001 + 0.001 | 1:10 | 69 |

Test Example 4

Five (5) parts of the present compound 1-3, 35 parts of a mixture of white carbon and ammonium polyoxyethylene alkyl ether sulfate (the weight ratio of 1:1) and 55 parts of water were mixed, and the mixture was then finely-ground by a wet grinding method to obtain a flowable comprising the present compound 1-3. Separately, the flowable comprising the present compound 2 was prepared according to the above-mentioned similar method except that the present compound 1-3 was used instead of the present compound 2.

Each of the flowable comprising the present compound 1-3 and the flowable comprising the present compound 2 was diluted with water and if necessary, the resultant dilute solutions were mixed each other such that each concentration of the respective compounds in the dilution solution was adjusted to the concentration indicated in Table 4, to prepare the dilution solutions, respectively.

A plastic pot was filled with soil, and thereto wheat (cultivar. Shirogane) was seeded, and the plants were grown in a greenhouse for ten days. The above-mentioned dilution solutions were sprayed to foliar parts so as to adhere adequately onto the surfaces of leaves of the above wheats. After spraying the dilute solution, the plants were air-dried, and one day after the application, an aqueous suspension of uredospores of Brown rust (Puccinia recondita) was inoculated by spraying thereto. After the inoculation, the plants were placed at 27° C. under humid condition for one day, and were then cultivated under lighting for ten days, and a lesion area was examined (hereinafter referred to as "lesion area of treated group").

Whereas, wheats were cultivated similarly to the treated group except that no foliage application of the above-mentioned agent solution was done, and Brown rust were inoculated, and the lesion area thereof was examined (hereinafter referred to as "lesion area of the untreated group").

From each of the lesion area of the treated group and the untreated group, respectively, the efficacy of the treated group was calculated by the following Equation 2.

From the test results, it was acknowledged that a synergistic effect was shown in the mixed-use group of the present compound 1-3 and the present compound 2 in comparison with the case of each of the single-use group of the above-mentioned compounds respectively.

Efficacy (%)=[1−(lesion area of the treated group)/(lesion area of the untreated group)]×100  Equation 2

TABLE 4

| Testing compound | Concentration in agent solution (ppm) | Mixing ratio (Present compound 1-3:Present compound 2) | Efficacy (%) |
|---|---|---|---|
| Present compound 1-3 | 0.01 | — | 70 |
| Present compound 1-3 | 0.002 | — | 35 |
| Present compound 2 | 0.02 | — | 55 |
| Present compound 2 | 0.001 | — | 15 |
| Present compound 1-3 + Present compound 2 | 0.01 + 0.001 | 1:0.1 | 100 |
| Present compound 1-3 + Present compound 2 | 0.002 + 0.02 | 1:10 | 100 |

The invention claimed is:

1. A composition for controlling a plant disease comprising a tetrazolinone compound represented by formula (1):

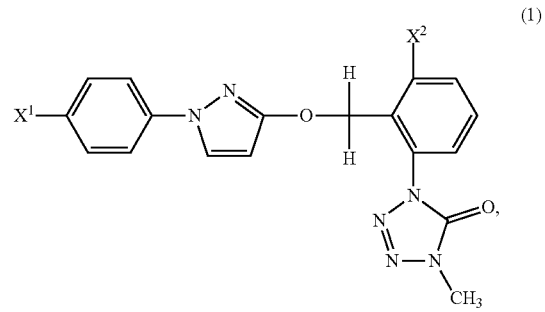

wherein
$X^1$ represents a chlorine atom, and
$X^2$ represents a methyl group, and
a carboxamide compound represented by formula (2):

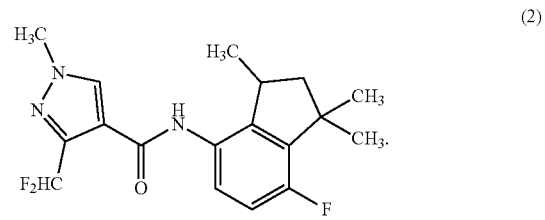 [SMILES: CC1CC(C)(C)c2c(F)ccc(NC(=O)c3cn(C)nc3C(F)F)c21]

2. The composition for controlling a plant according to claim 1, wherein a weight ratio of the tetrazolinone compound to the carboxamide compound is 1:0.0125 to 1:500.

3. A method for controlling a plant disease, comprising applying an effective amount of a tetrazolinone compound represented by formula (1):

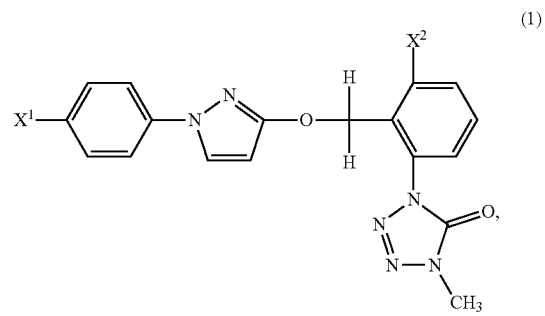

wherein
$X^1$ represents a chlorine atom, and
$X^2$ represents a methyl group, and
an effective amount of a carboxamide compound represented by formula (2):

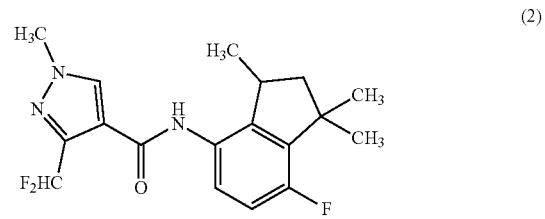 [SMILES: CC1CC(C)(C)c2c(F)ccc(NC(=O)c3cn(C)nc3C(F)F)c21]

to a plant or soil for cultivating the plant.

4. A method for controlling a plant disease, comprising applying an effective amount of a tetrazolinone compound represented by formula (1):
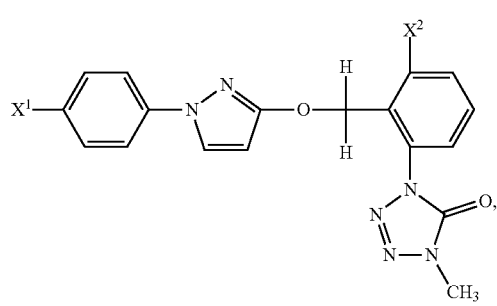
(1)
wherein
 X¹ represents a chlorine atom, and
 X² represents a methyl group, and
an effective amount of a carboxamide compound represented by formula (2):
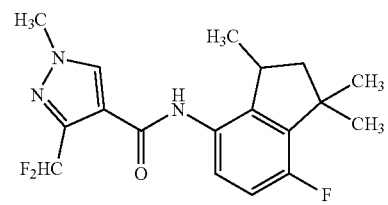
(2)
to a seed.
* * * * *